United States Patent
Robinson et al.

(12)
(10) Patent No.: US 6,232,065 B1
(45) Date of Patent: May 15, 2001

(54) ANALYSIS OF GENE FAMILY EXPRESSION

(75) Inventors: Daniel R. Robinson, Cleveland; Hsing-Jien Kung, Chagrin Falls, both of OH (US)

(73) Assignee: Case Western Reserve University, Cleveland, OH (US)

(*) Notice: Subject to any disclaimer, the term of this patent is extended or adjusted under 35 U.S.C. 154(b) by 0 days.

(21) Appl. No.: 09/073,407

(22) Filed: May 6, 1998

(51) Int. Cl.[7] .............................. C12Q 1/68; C12P 19/34; C01H 21/02; C07H 21/04; C12N 15/00

(52) U.S. Cl. ............................ 435/6; 435/91.2; 536/23.1; 536/24.3; 935/76; 935/77; 935/78

(58) Field of Search ..................... 435/6, 91.2; 536/23.1, 536/24.3; 935/76, 77, 78

(56) References Cited

U.S. PATENT DOCUMENTS

| | | |
|---|---|---|
| 4,683,195 | 7/1987 | Mullis et al. . |
| 4,683,202 | 7/1987 | Mullis . |
| 4,965,188 | 10/1990 | Mullis et al. . |
| 5,213,961 | 5/1993 | Bunn et al. .............................. 435/6 |
| 5,476,774 | 12/1995 | Wang et al. ........................ 435/91.2 |
| 5,599,666 * | 2/1997 | Schumm et al. ......................... 435/6 |

OTHER PUBLICATIONS

The Stratagene Catalog, Gene Characterization Kits, (1988) p.39.
Kohout et al., Use of PCR–based Method to Characterize Protein Kinase C Isoform Exprression in Cardiac Cells. Am. J. Physiology 264 : C1350–C1359 (1993).*
Buck et al., A Greneral Method for Quantitative PCR Analysis of mRNA Levels for Members of Gene Families: Application to GABA Receptor Subunits. Biotechniques 11(5) : 636–641 (1991).*
Madewell et al., Canine and Bovine Ras Family Expression Detected and Discriminated by use of Polymerase Chain Reaction. Anticancer Research 9 : 1743–1750 (1989).*
Levesque et al., Determination of Changes in Specific Gene Expression by Reverse Transcription PCR using Interspecies mRNAs as Internal Standards. Biotechniques 17(4) : 738–741 (1994).*
Kuwata et al., Differential Expression of Protein Tyrosine Kinases in the Cortical and Medullary Thymic Epithelial Cell Lines. Biochem. and Biophys. Research Communications. 213(3) : 768–773 (1995).*
Gene Characterization Kits. The Stratagene Catalog. p.39 (1988).*
Adams et al. (1993) "Rapid cDNA sequencing (expressed sequence tags) from a directionally cloned human infant brain cDNA library," Nature Genetics 4:373.
Adams et al. (1991) "Complementary DNA Sequencing: Expressed Sequence Tags and Human Genome Project," Science 252:1651.

Anderson and Young (1985) "Quantitative Filter Hybridization" in *Nucleic Acids Hybridization.*
Bauer et al. in *PCR Methods and Applications,* Cold Spring Harbor Lab. Press, Plaiview, NY, Supplement, pp. S97–S108 (1994).
Bertioli et al. (1995) "An analysis of differential display shows a strong bias towards high copy number mRNAs," Nucleic Acids Res. 23:4520.
Chee et al. (1996) "Accessing Genetic Information with High–Density Arrays," Science 274:610.
Chenchik et al. (1996) "Full–Length cDNA Cloning and Determination of mRNA 5' and 3' Ends by Amplification of Adaptor–Ligated cDNA," BioTechniques 21:526.
Chirgwin et al. (1979) "Isolation of Biologically Active Ribonucleic Acid from Sources Enriched in Ribonuclease," Biochemistry 18:5294.
DeRisi et al. (1996) "Use of a cDNA microarray to analyse gene expression patterns in human cancer," Nat. Genet. 14:457.
D'Esposito et al. (1994) "BLOCK–based PCR markers to find gene family members in human and comparative genome analysis," Hum. Mol. Genet. 3:735.
Diatchenko et al. (1996) "Suppression subtractive hybridization: A method for generating differentially regulated or tissue specific cDNA probes and libraries," Proc. Natl. Acad. Sci. 93:6025.
Frohman et al. (1988) "Rapid production of full–length cDNAs from rare transcripts: Amplification using a single gene–specific oligonucleotide primer," Proc. Natl. Acad. Sci. 85:8998.
Gerlach et al. (1986) "Multidrug resistance," Cancer Surveys 5:25.
Goldie and Coldman (1984) "The Genetic Origin of Drug Resistance in Neoplasms: Implications for Systemic Therapy," Cancer Research 44:3643.
Gress et al. (1996) "A pancreatic cancer–specific expression profile," Oncogene 13:1819.
Haag et al. (1994) "Effects of Primer Choice and Source of Taq DNA Polymerase on the Banding Patterns of Differential Display RT–PCR," Biotechniques 17:226.
Hanks and Lindberg (1991) "Use of Degenerate Oligonucleotide Probes to Identify Clones that Encode Protein Kinases," Methods Enzymol. 200:525.
Hanks and Quinn (1991) "Protein Kinase Catalytic Domain Sequence Database: Identification of Conserved Features of Primary Structure and Classification of Family Members," Methods Enzymol. 200:38.

(List continued on next page.)

*Primary Examiner*—Ethan Whisenant

(57) ABSTRACT

The present invention relates to methods and compositions for characterizing the expression patterns of genes and gene families. Specifically, the present invention provides means to generate and monitor gene expression profiles resulting from cellular and physiological changes such that the expression patterns of individual genes or groups of genes can be readily identified and characterized.

19 Claims, No Drawings

OTHER PUBLICATIONS

Hanks et al. (1988) "The Protein Kinase Family: Conserved Features and Deduced Phylogeny of the Catalytic Domains," Science 241:42.

Hunter (1987) "A Thousand and One Protein Kinases," Cell 50:823.

Ikonomov et al. (1996) "Differential Display Protocol with Selected Primers That Preferentially Isolates mRNAs of Moderate to Low Abundance in a Microscopic System," BioTechniques 20:1030.

Lanzi et al. (1992) "Identification of the product of two oncogenic rearranged forms of the RET proto–oncogene in papillary thyroid carcinomas," Oncogene 7:2189.

Liang et al. (1992) "Differential Display and Cloning of Messenger RNAs from Human Breast Cancer versus Mammary Epithelial Cells," Cancer Res. 52:6966.

Liang and Pardee (1992) "Differential Display of Eukaryotic Messenger RNA by Means of the Polymerase Chain Reaction," Science 257:967.

Ling and King (1995) "Mitogenic Signals and Transforming Potential of Nyk, a Newly Identified Neural Cell Adhesion Molecules–Related Receptor Tyrosine Kinase," Mol. Cell Biol. 15:6582.

McIndoe et al. (1996) "An analysis of the dynamic range and linearity of an infrared DNA sequencer," Electophoresis 17:652.

Maskos and Southern (1993) "A study of oligonucleotide reassociation using large arrays of oligonucleotides synthesised on a glass support," Nucleic Acids Res. 21:4663.

Pietu et al. (1996) "Novel Gene Transcripts Preferentially Expressed in Human Muscles Revealed by Quantitative Hybridication of a High Density cDNA Array," Genome Res. 6:492.

Robinson et al. (1996) "A tyrosine kinase profile of prostate carcinoma," Proc. Natl. Acad. Sci. 93:5958.

Sambrook et al. in *Molecular Cloning: A Laboratory Manual,* Cold Spring Harbor Press, NY, pp 9.31–9.58, 1989.

Schena et al. (1995) "Quantitative Monitoring of Gene Expression Patterns with a Complementary DNA Microarray," Science 270:467.

Schena et al. (1996) "Parallel human genome analysis: Microarray–based expression monitoring of 1000 genes," Proc. Natl. Acad. Sci. 93:10614.

Sompayrac et al. (1995) "Overcoming limitations of the mRNA differential display technique," Nucleic Acids Res. 23:4738.

Velculescu et al. (1995) "Serial Analysis of Gene Expression," Science 270:484.

Wainstein et al. (1994) "CWR22: Androgen–dependent Xenograft Model Derived from a Primary Human Prostatic Carcinoma," Cancer Res. 54:6049.

Broude et al., "Differential display of genome subsets containing specific interspersed repeats," Proc. Natl. Acad. Sci., 94:4548–4553 [1997].

Hatchwell, "Improving PCR specificity by multiple pre–digestion," TIG 12:460 [1996].

Visser et al., "Haemopoietic growth factor tyrosine kinase receptor expression profiles in normal haemopoiesis," Br. J. of Haematology 94:236–241 [1996].

Lai and Lemke, "An extended family of protein–tyrosine kinase genes differentially expressed in the vertebrate nervous system," Neuron 6:691–704 [1991].

Henikoff et al., "Gene families: The taxonomy of protein paralogs and chimeras," Science 278:609–614 [1997].

Burgart et al., "Multiplex polymerase chain reaction," Modern Pathology 5:320–323 [1992].

Wilks, "Two putative protein–kinases identified by application of the polymerase chain reaction," Proc. Natl. Acad. Sci. 86:1603–1607 [1989].

Tatusov, et al., "A genomic perspective on protein families," Science 278:631–637 [1997].

Gashler and Sukhatme, "Early growth response protein 1 (Egr–1): Prototype of a zinc–finger family transcription factors," Progress in Nucleic Acids Research 50:191–199 [1995].

McClelland et al., "RNA fingerprinting and differential display using arbitrarily primed PCR," TIG 11:242–246 [1995].

Lisitsyn et al., "Cloning the differences between two complex genomes," Science 259:946–951 [1993].

* cited by examiner

SEQUENCE LISTING

<160> NUMBER OF SEQ ID NOS: 13

<210> SEQ ID NO 1
<211> LENGTH: 27
<212> TYPE: PRT
<213> ORGANISM: Artificial Sequence
<220> FEATURE:
<223> OTHER INFORMATION: Description of Artificial Sequence:  Synthetic

<400> SEQUENCE: 1

Cys Cys Ala Gly Gly Thr Cys Ala Cys Cys Ala Ala Arg Arg Thr Trp
 1               5                  10                  15

Asp Cys Arg Gly Ala Tyr Thr Thr Tyr Gly Gly
            20                  25

<210> SEQ ID NO 2
<211> LENGTH: 27
<212> TYPE: PRT
<213> ORGANISM: Artificial Sequence
<220> FEATURE:
<223> OTHER INFORMATION: Description of Artificial Sequence:  Synthetic

<400> SEQUENCE: 2

Cys Cys Ala Gly Gly Thr Cys Ala Cys Cys Ala Ala Arg Arg Thr Trp
 1               5                  10                  15

Asp Cys Tyr Gly Ala Tyr Thr Thr Tyr Gly Gly
            20                  25

<210> SEQ ID NO 3
<211> LENGTH: 27
<212> TYPE: PRT
<213> ORGANISM: Artificial Sequence
<220> FEATURE:
<223> OTHER INFORMATION: Description of Artificial Sequence:  Synthetic

<400> SEQUENCE: 3

Cys Cys Ala Gly Gly Thr Cys Ala Cys Ala Ala Arg Arg Thr Trp
 1               5                   10                  15

Trp Gly Tyr Gly Ala Tyr Thr Thr Tyr Gly Gly
             20                  25

<210> SEQ ID NO 4
<211> LENGTH: 27
<212> TYPE: PRT
<213> ORGANISM: Artificial Sequence
<220> FEATURE:
<223> OTHER INFORMATION: Description of Artificial Sequence: Synthetic

<400> SEQUENCE: 4

Cys Cys Ala Gly Gly Thr Cys Ala Cys Ala Ala Arg Arg Thr Trp
 1               5                   10                  15

Gly Gly Asn Gly Ala Tyr Thr Thr Tyr Gly Gly
             20                  25

<210> SEQ ID NO 5
<211> LENGTH: 27
<212> TYPE: PRT
<213> ORGANISM: Artificial Sequence
<220> FEATURE:
<223> OTHER INFORMATION: Description of Artificial Sequence: Synthetic

<400> SEQUENCE: 5

Cys Cys Ala Gly Gly Thr Cys Ala Cys Ala Ala Arg Arg Thr Ile
 1               5                   10                  15

Asp Cys Asn Gly Ala Tyr Thr Thr Tyr Gly Gly
             20                  25

<210> SEQ ID NO 6
<211> LENGTH: 27
<212> TYPE: PRT
<213> ORGANISM: Artificial Sequence
<220> FEATURE:
<223> OTHER INFORMATION: Description of Artificial Sequence: Synthetic

<400> SEQUENCE: 6

Cys Cys Ala Gly Gly Thr Cys Ala Cys Ala Ala Arg Arg Thr Thr
 1               5                   10                  15

Asp Cys Asn Gly Ala Tyr Thr Thr Tyr Gly Gly
             20                  25

<210> SEQ ID NO 7
<211> LENGTH: 27
<212> TYPE: PRT
<213> ORGANISM: Artificial Sequence
<220> FEATURE:
<223> OTHER INFORMATION: Description of Artificial Sequence: Synthetic

<400> SEQUENCE: 7

Cys Cys Ala Gly Gly Thr Cys Ala Cys Ala Ala Arg Arg Thr Ile
 1               5                   10                  15

Trp Gly Tyr Gly Ala Tyr Thr Thr Tyr Gly Gly
             20                  25

<210> SEQ ID NO 8
<211> LENGTH: 27
<212> TYPE: PRT
<213> ORGANISM: Artificial Sequence
<220> FEATURE:
<223> OTHER INFORMATION: Description of Artificial Sequence: Synthetic

<400> SEQUENCE: 8

Cys Cys Ala Gly Gly Thr Cys Ala Cys Cys Ala Ala Arg Arg Thr Thr
1               5                   10                  15

Trp Gly Tyr Gly Ala Tyr Thr Thr Tyr Gly Gly
            20                  25

<210> SEQ ID NO 9
<211> LENGTH: 26
<212> TYPE: PRT
<213> ORGANISM: Artificial Sequence
<220> FEATURE:
<223> OTHER INFORMATION: Description of Artificial Sequence: Synthetic

<400> SEQUENCE: 9

Cys Ala Cys Ala Gly Gly Thr Thr Ala Cys Cys Arg His Ala Asn Gly
1               5                   10                  15

Met Cys Cys Ala Ala Ala Cys Arg Thr Cys
            20                  25

<210> SEQ ID NO 10
<211> LENGTH: 26
<212> TYPE: PRT
<213> ORGANISM: Artificial Sequence
<220> FEATURE:
<223> OTHER INFORMATION: Description of Artificial Sequence: Synthetic

<400> SEQUENCE: 10

Cys Ala Cys Ala Gly Gly Thr Thr Ala Cys Cys Arg His Ala Asn Gly
1               5                   10                  15

Met Cys Cys Ala Cys Ala Cys Arg Thr Cys
            20                  25

<210> SEQ ID NO 11
<211> LENGTH: 26
<212> TYPE: PRT
<213> ORGANISM: Artificial Sequence
<220> FEATURE:
<223> OTHER INFORMATION: Description of Artificial Sequence: Synthetic

<400> SEQUENCE: 11

Cys Ala Cys Ala Gly Gly Thr Thr Ala Cys Cys Arg His Ala Asn Gly
1               5                   10                  15

Met Cys Cys Ala Gly Ala Cys Arg Thr Cys
            20                  25

<210> SEQ ID NO 12
<211> LENGTH: 26
<212> TYPE: PRT
<213> ORGANISM: Artificial Sequence
<220> FEATURE:
<223> OTHER INFORMATION: Description of Artificial Sequence: Synthetic

<400> SEQUENCE: 12

Cys Ala Cys Ala Gly Gly Thr Thr Ala Cys Cys Arg His Ala Asn Gly
1               5                   10                  15

Met Cys Cys Ala Thr Ala Cys Arg Thr Cys
            20                  25

<210> SEQ ID NO 13
<211> LENGTH: 26
<212> TYPE: PRT
<213> ORGANISM: Artificial Sequence
<220> FEATURE:
<223> OTHER INFORMATION: Description of Artificial Sequence: Synthetic -continued

```
<400> SEQUENCE: 13

Cys Ala Cys Ala Gly Gly Thr Thr Ala Cys Cys Arg His Ala Arg Cys
1               5                   10                  15

Thr Cys Cys Ala Asn Ala Cys Arg Thr Cys
                20                  25
```

ANALYSIS OF GENE FAMILY EXPRESSION

FIELD OF THE INVENTION

The present invention relates to methods and compositions for characterizing the expression patterns of genes and gene families. Specifically, the present invention provides means to generate and monitor gene expression profiles resulting from cellular and physiological changes such that the expression patterns of individual genes or groups of genes can be readily identified and characterized.

BACKGROUND OF THE INVENTION

Developing methods to detect molecular alterations in biological samples is key to increasing our knowledge about the causes of diseases, the processes of cellular development and differentiation, and other physiological and cellular events, and in developing tools to detect, treat, alter, and monitor these conditions. Perhaps the most significant alteration that can occur in a cell is in its pattern of gene transcription, which exerts profound control on protein levels and activities. Thus, the detection of changes in mRNA levels in the thousands of genes expressed by a single cell is an important goal for many research programs.

With the extensive amount of cDNA sequence information available through the efforts of genome sequencing projects, as well as those of thousands of individual laboratories, it is becoming increasingly imperative to develop technologies that can utilize this information to study the patterns of gene expression in both development and disease. Most human cancers, for example, are the result of genetic changes that result in alterations in the profile of expressed genes within a cell. Methods that can rapidly and accurately measure the expression levels of thousands of genes will play an essential role in furthering our understanding of the causes and nature of progression of human cancers, detecting and monitoring cancers and others diseases, and identifying and developing treatment methods for the diseases.

Several approaches have been developed in recent years in an attempt to achieve reliable, economical measurement of patterns and levels of gene expression. These include sequencing-based methods such as expressed sequence tag (EST) databases (See e.g., Adams et al., Nature Genetics 4, 373 [1993]) and SAGE (See e.g., Velculescu et al., Science 270, 484 [1995]), PCR based methods such as differential display (See e.g., Liang et al., Cancer Res. 52, 6966 [1992]; and Liang and Pardee, Science 257, 967 [1992]), and methods based on hybridization to microarrays of EST clones or oligonucleotides (See e.g., Chee et al., Science 274, 610 [1996]; DeRisi et al., Nat. Genet. 14, 457 [1996]; Gress et al., Oncogene 13, 1819 [1996]; Maskos and Southern, Nucleic Acids Res. 21, 4663 [1993]; Pietu et al., Genome Res. 6, 492 [1996]; Schena et al., Science 270, 467 [1995]; and Schena et al., Proc. Natl. Acad. Sci. 93, 10614 [1996]) or by subtractive hybridization (See e.g., Diatchenko et al., Proc. Natl. Acad. Sci. 6025 [1996]). The strengths and weaknesses of each of these technologies is assessed below.

Partial sequencing of randomly selected cDNA clones directly from cDNA libraries (i.e., producing expressed sequence tags—ESTs) has been used as a means of identifying new genes and analyzing the expression pattern of tissues and cell lines (See e.g., Adams et al., Science 252, 1651 [1991]). In these methods, total mRNA is reverse transcribed to produce cDNA. The cDNA are hybridized to random primers and sequenced (typically with automated sequencers), with ESTs of longer than 150 bp providing the best data for comparison to sequence databases. The sequence information can be compared to available sequence databases to characterize the cDNA as being derived from a known or novel gene. However, sequencing ESTs is very labor intensive, time consuming, and expensive. As a means of monitoring gene expression, the value of the data depends on the extent to which sequence information is already available (i.e., the method may indicate that a previously identified gene is expressed in a given tissue but will not provide information about the expression of related genes that have yet to be identified and catalogued).

Serial analysis of gene expression (SAGE) provides another sequencing-based method to characterizes expression patterns (Velculescu et al., supra). In the SAGE technique, RNA is reverse transcribed to produce cDNA copies of the transcripts. The cDNA is then cleaved with a restriction enzyme that cuts each transcript at least once. The 3' portion of the restriction products (containing the poly-A tail) are isolated using streptavidin beads. The samples are divided into two portions and the free restriction ends are ligated to one of two linkers containing a type IIS restriction site. IIS restriction enzymes cleave at a defined distance from their recognition sites (i.e., as opposed to cleaving directly at the recognition site). The linkers are designed to produce IIS cleavage products that contain only a short piece (i.e., the tag) of the original cDNA, ligated to the linker. Blunt ends are produced and the two pools are ligated together creating a "ditag" with the two types of linkers on either end and the short cDNA tags in the center. The ditags are then PCR amplified using primers that are complementary to sequence within the two linkers. The PCR products are then cloned and manually sequenced, before comparing to sequence databases or SAGE experiments from other samples. Although SAGE provides a means to compare gene expression patterns, its dependance on cloning and sequencing make it labor intensive. Furthermore, SAGE does not allow the study of specific genes or gene families, but instead screens all expressed transcripts.

A PCR-based approach for identifying gene expression differences between samples is the differential display of mRNAs using arbitrarily primed polymerase chain reaction (DDRT-PCR). The polymerase chain reaction is described by Mullis et al., in U.S. Pat. Nos. 4,683,195, 4,683,202, and 4,965,188, hereby incorporated by reference. Briefly, the PCR process consists of introducing a molar excess of two oligonucleotide primers to the cDNA mixture containing the desired target sequence (e.g., a poly-T primer that hybridizes to the poly-A tail of mRNAs and a random oligomer). The two primers are complementary to their respective strands of the double-stranded sequence. The mixture is denatured and then allowed to hybridize. Following hybridization, the primers are extended with a thermostable DNA polyerase so as to from complementary strands. The steps of denaturation, hybridization, and polymerase extension can be repeated as often as needed to obtain a relatively high concentration of a segment of the desired target sequence.

In the case of DDRT-PCR, the target is mRNA; the mRNA is, however, treated with reverse transcriptase in the presence of oligo(dT) primers to make cDNA prior to the PCR process. The PCR is carried out with random primers in combination with the oligo(dT) primer used for cDNA synthesis. In theory, since only cDNA (i.e., derived from mRNA) is amplified, only the expressed genes are amplified. Where two samples are to be compared, the amplified products are placed in side-by-side lanes of a gel; following electrophoresis, the products can be compared or "differentially displayed."

DDTR-PCR has a number of drawbacks. The use of arbitrary random primers can cause faint banding at essentially every position of the gel, and there is usually a high level of false positives (See e.g, Bauer et al., *PCR Methods and Applications*, Cold Spring Harbor Lab. Press, Plainview, N.Y., Supplement, pp. S97–S108 [1994]). Also, the process is generally biased toward high-copy number genes (See e.g., Bertioli et al., Nucleic Acids Res. 23, 4520 [1995]) and is often inappropriate for experiments where only a few genes vary in expression (See e.g., Sompayac et al., Nucleic Acids Res. 23, 4738 [1995]). Lastly, practitioners often complain about difficulties in reproducing banding patterns.

There have been some attempts to remedy these problems. For example, E. Haag et al. (Biotechniques 17, 226 [1994]) describes an improved DDRT-PCR method, whereby the use of the standard oligo-dT primer in the PCR step is omitted to decrease the faint banding at essentially every position of the electrophoresis gel. Instead, a second arbitrary primer was utilized in PCR. Another example is O. C. Ikonomov el al. (Biotechiques 20, 1030 [1996]), describing the use of a modified DDRT-PCR protocol to increase bias towards moderate to low abundance transcripts. The authors utilized experimentally selected primer pairs directed at known coding sequences that avoid amplification of highly abundant ribosomal and mitochondrial transcripts. While such efforts have improved DDRT-PCR, the process remains unsatisfactory because of the continued amplification of material that is not of interest.

A significant disadvantage to current DDRT-PCR techniques is the laborious steps required to characterized differentially expressed samples. Interesting bands must be excised from the gel and cloned. Such cloning is non-trivial, as PCR products tend to have a single adenosine residue overhang, requiring processing before cloning into traditional vectors, or requiring cloning into T-vectors (i.e., vectors containing a single thymine overlap), which is inefficient. Following cloning, the insert must be sequenced and compared to nucleic acid data bases to determine its identity or novelty. Such cloning and sequencing is time consuming, labor intensive, and expensive.

Other approaches to analyze gene expression patterns involve technologies utilizing high-density DNA arrays placed on computer chips. The technology is being applied to the study of gene expression, genetic linkage, and genetic variability. For example, Chee et al. (Chee et al., supra) describe the use of DNA arrays on computer chips to simultaneously analyze the entire human mitochondrial genome. Arrays containing 135,000 probes, representing the entire human mitochondrial genome, were generated on chips. Within minutes, experimental DNA was hybridized to the chip to detect sequence polymorphisms with single-base resolution. Although the method is accurate and efficient, testing is limited by the generation of the DNA arrays. Each time a new system is to be tested, an array must be generated, an extremely time consuming, technically complex, and expensive process.

Several subtractive hybridization methods have also been used to characterize cDNA levels to identify differences between biological samples. In one methods, the so-called "subtractive cDNA library" method (See generally, Ausubel et al, *Current Protocols in Molecular Biology*, Section 5.8.9 [1990]), a subracted cDNA library is generated or obtained (ATCC or Stratagene) containing cDNA clones corresponding to mRNAs present in one sample and not present in another (e.g., present in a particular species, tissue, or cell and present in another species, tissue or cell). In the protocol, cDNA containing the gene(s) of interest ("+cDNA") is prepared with restriction enzymes ends and the cDNA not containing the gene(s) of interest ("−cDNA") is prepared with blunt ends. The +cDNA is mixed with a 50-fold excess of −cDNA inserts and the mixture is heated to make the DNA single-stranded. Thereafter, the mixture is cooled to allow for hybridization. Annealed cDNA inserts are ligated to a vector and transfected. In theory, the only +cDNA likely to be double-stranded with a the restriction enzyme sites at each end are those not hybridized to something in the −cDNA preparation (i.e., where a complementary sequence is in the −cDNA preparation, the sequence will not be transfected). Thus, only sequences unique to the +cDNA preparation will be cloned and amplified.

There are several significant disadvantages to this technique. First, it can be very tedious. For example, if no "+" and "−" cDNA libraries are available for the samples to be studied, they must first be made or cDNA must be sythesized, requiring extra days or weeks. Even when cDNA libraries are available, the protocol still requires several days. Second, library production with small amounts of cDNA is technically very difficult. Also, since relatively few recombinants are obtained after subtraction, this protocol is only effective when using library vectors that allow high cloning efficiency. Third, clones containing reiterated sequences (e.g., an Alu repeat in the 3' untranslated region) are eliminated from the library, misrepresenting the presence of clones containing such sequences.

Some of the disadvantages of the subtractive cDNA library techniques have been overcome using a PCR-based "supression subtractive hybridization" technique (Diatchenko et al., supra). The method is used to selectively amplify target cDNA fragments and simultaneously suppress nontarget DNA amplification, overcoming the problem of differences in mRNA abundance. The method eliminates the need to physically separate single and double stranded molecules. However, as this method still requires "+" and "−" cDNA samples, it remains a tedious procedure if samples are not available. A major drawback of all subtractive hybridization methods is the need to clone and sequence desired fragments in order to identify and characterize them.

What is needed is an inexpensive, easy to use, time efficient, and reliable method for distinguishing between the expression of genes in two or more biological samples. Such a method should also promote followup analysis once a gene of interest is identified. Ideally, such analysis would avoid time consuming steps such as cloning and sequencing.

SUMMARY OF THE INVENTION

The present invention relates to methods and compositions for characterizing the expression patterns of genes and gene families. Specifically, the present invention provides means to generate and monitor gene expression profiles resulting from cellular and physiological changes such that the expression patterns of individual genes or groups of genes can be readily identified and characterized.

The present invention employs oligonucleotide primers targeting conserved regions or motifs within each expressed gene of a multigene family. In one embodiment, the present invention contemplates first and second oligonucleotide primers, said first oligonucleotide primer specific for a first conserved region and said second oligonucleotide primer specific for a second conserved region, said first and second conserved regions separated in each gene by a distance, said distance varying between 1 and 2000 bases, and more preferably 80 to 1000 bases.

In one embodiment, the present invention contemplates a method, comprising: a) providing: i) a sample containing nucleic acid, ii) a first primer having a sequence of which at least a portion is at least partially complementary to a first conserved region (defined by a first natural coding sequence found on two or more genes of a multigene family), iii) a second primer having a sequence of which at least a portion is at least partially complementary to a second conserved region (defined by a second natural coding sequence found on two or more genes of a multigene family), said first and second conserved regions separated in each gene by a distance, said distance varying between a minimum distance and a maximum distance (maximum and minimum distances being defined by comparing the distances between priming sites in all known members of the gene family of interest), said maximum distance differing from said minimum distance by less than 40% of said maximum distance (and more preferably less than 20%, and still more preferably less than 10%) and iv) a polymerase and PCR reagents; b) preparing said nucleic acid from said sample under conditions so as to produce amplifiable nucleic acid; c) amplifying said nucleic acid with said first and second primers, said polymerase, and said PCR reagents under conditions such that amplified product is generated; and d) isolating amplified product in a size range, said range defined by a lower end and a higher end, said lower end defined by approximately said minimum distance (e.g., within 30 bases, plus or minus) and said higher end defined by approximately said maximum distance.

The present invention can be used with particular success when comparing samples. In one embodiment, the present invention contemplates a method of analyzing expressed genes in biological samples, comprising: a) providing: i) two samples containing mRNA, ii) a first primer having a sequence of which at least a portion is at least partially complementary to a first conserved region (defined by a first natural coding sequence found on two or more genes of a multigene family), iii) a second primer having a sequence of which at least a portion is at least partially complementary to a second conserved region (defined by a second natural coding sequence found on two or more genes of a multigene family), said first and second conserved regions separated in each gene by a distance, said distance varying between a minimum distance and a maximum distance among said genes in said multigene family, said maximum distance differing from said minimum distance by less than 40% of said maximum distance (and more preferably less than 20%, and still more preferably less than 10%) and, iv) a polymerase and PCR reagents; b) treating said mRNA of each of said two samples under conditions so as to produce amplifiable DNA from each sample; c) amplifying said DNA from each sample with said first and second primers, said polymerase and said PCR reagents under conditions such that amplified product is generated from each of said two samples; d) electrophoresing said amplified product on a gel; and e) isolating amplified product in a size range, said range defined by a lower end and a higher end, said lower end defined by approximately said minimum distance and said higher end defined by approximately said maximum distance.

The comparison can be made between cells of similar type. On the other hand, dissimilar samples can be usefully compared. It is not intended that the present invention be limited by the number of samples compared. Clinical samples are specifically contemplated within the scope of the present invention.

The present invention contemplates the primers of the present invention as unique compositions. The present invention also contemplates kits containing these novel compositions.

DEFINITIONS

To facilitate an understanding of the present invention, a number of terms and phrases are defined below:

"Nucleic acid sequence" and "nucleotide sequence" as used herein refer to an oligonucleotide or polynucleotide, and fragments or portions thereof, and to DNA or RNA of genomic or synthetic origin that may be single- or double-stranded, and represent the sense or antisense strand.

As used herein, the terms "complementary" or "complementarity" are used in reference to "polynucleotides" and "oligonucleotides" (which are interchangeable terms that refer to a sequence of nucleotides) related by the base-pairing rules. For example, the sequence "C-A-G-T," is complementary to the sequence "G-T-C-A." Complementarity can be "partial" or "total." "Partial" complementarity is where one or more nucleic acid bases is not matched according to the base pairing rules. "Total" or "complete" complementarity between nucleic acids is where each and every nucleic acid base is matched with another base under the base pairing rules. The degree of complementarity between nucleic acid strands has significant effects on the efficiency and strength of hybridization between nucleic acid strands. This is of particular importance in amplification reactions, as well as detection methods which depend upon binding between nucleic acids.

The terms "homology" and "homologous" as used herein in reference to nucleotide sequences refer to a degree of complementarity with other nucleotide sequences. There may be partial homology or complete homology (i.e., identity). A nucleotide sequence that is partially complementary, i.e., "substantially homologous," to a nucleic acid sequence is one that at least partially inhibits a completely complementary sequence from hybridizing to a target nucleic acid sequence. The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (i.e., the hybridization) of a completely homologous sequence to a target sequence under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target sequence that lacks even a partial degree of complementarity (e.g., less than about 30% identity); in the absence of non-specific binding the probe will not hybridize to the second non-complementary target.

Low stringency conditions comprise conditions equivalent to binding or hybridization at 42° C. in a solution consisting of 5×SSPE (43.8 g/l NaCl, 6.9 g/l $NaH_2PO_4 \cdot H_2O$ and 1.85 g/l EDTA, pH adjusted to 7.4 with NaOH), 0.1% SDS, 5×Denhardt's reagent [50×Denhardt's contains per 500 ml: 5 g Ficoll (Type 400, Pharmacia), 5 g BSA (Fraction V; Sigma)] and 100 µg/ml denatured salmon sperm DNA followed by washing in a solution comprising 5×SSPE, 0.1% SDS at 42° C. when a probe of about 500 nucleotides in length is employed.

The art knows well that numerous equivalent conditions may be employed to comprise low stringency conditions; factors such as the length and nature (DNA, RNA, base composition) of the probe and nature of the target (DNA, RNA, base composition, present in solution or immobilized, etc.) and the concentration of the salts and other components (e.g., the presence or absence of formamide, dextran sulfate, polyethylene glycol), as well as components of the hybridization solution may be varied to generate conditions of low stringency hybridization different from, but equivalent to, the above listed conditions. In addition, the art knows conditions that promote hybridization under conditions of high stringency (e.g., increasing the temperature of the hybridization and/or wash steps, the use of formamide in the hybridization solution, etc.).

When used in reference to a double-stranded nucleic acid sequence such as a cDNA or genomic clone, the term "substantially homologous" refers to any probe that can hybridize to either or both strands of the double-stranded nucleic acid sequence under conditions of low stringency as described above.

When used in reference to a single-stranded nucleic acid sequence, the term "substantially homologous" refers to any probe that can hybridize (i.e., it is the complement of the single-strainded nucleic acid sequence under conditions of low stringency as described above.

As used herein, the term "conserved region" and more specifically "conserved region of a gene in a multigene family" refers to a segment of nucleotide sequence of a gene or amino acid sequence of a protein that is significantly similar between members of gene families. The degree of similarity can vary. In some cases the conserved regions will be identical between family members. In some cases the nucleotide sequence may vary significantly but still encode for amino acid segments that are conserved between family members (e.g., such situation can arise when more than one codon encodes a particular amino acid). Typically, sequences that are less than 30% homologous between samples are considered non-conserved. Similarity greater than 70% homology is typically considered highly conserved.

As used herein, the term "consensus sequence" refers to the bases most often found at any given position when comparing a large number of similar nucleotide sequences. For example, the consensus DNA sequence located approximately 10 base pairs upstream of the RNA start site in *Escherichia coli* transcriptional promoters is TATAAT although not all *E. coli* promoter sequences conform exactly to this sequence.

As used herein, the term "hybridization" is used in reference to the pairing of complementary nucleic acids using any process by which a strand of nucleic acid joins with a complementary strand through base pairing to form a hybridization complex. Hybridization and the strength of hybridization (i.e., the strength of the association between the nucleic acids) is impacted by such factors as the degree of complementarity between the nucleic acids, stringency of the conditions involved, the $T_m$ of the formed hybrid, and the G:C ratio within the nucleic acids.

As used herein the term "hybridization complex" refers to a complex formed between two nucleic acid sequences by virtue of the formation of hydrogen bonds between complementary G and C bases and between complementary A and T bases; these hydrogen bonds may be further stabilized by base stacking interactions. The two complementary nucleic acid sequences hydrogen bond in an antiparallel configuration. A hybridization complex may be formed in solution (e.g., $C_0t$ or $R_0t$ analysis) or between one nucleic acid sequence present in solution and another nucleic acid sequence immobilized to a solid support (e.g., a nylon membrane or a nitrocellulose filter as employed in Southern and Northern blotting, dot blotting or a glass slide as employed in in situ hybridization, including FISH [fluorescent in situ hybridization]).

As used herein, the term "$T_m$" is used in reference to the "melting temperature." The melting temperature is the temperature at which a population of double-stranded nucleic acid molecules becomes half dissociated into single strands. The equation for calculating the $T_m$ of nucleic acids is well known in the art. As indicated by standard references, a simple estimate of the $T_m$ value may be calculated by the equation: $T_m=81.5+0.41$ (% G+C), when a nucleic acid is in aqueous solution at 1 M NaCl [see e.g., Anderson and Young, Quantitative Filter Hybridization, in *Nucleic Acid Hybridization* (1985)]. Other references include more sophisticated computations that take structural as well as sequence characteristics into account for the calculation of $T_m$.

As used herein the term "stringency" is used in reference to the conditions of temperature, ionic strength, and the presence of other compounds such as organic solvents, under which nucleic acid hybridizations are conducted. "Stringency" typically occurs in a range from about $T_m-5°$ C. (5° C. below the $T_m$ of the probe) to about 20° C. to 25° C. below $T_m$. As will be understood by those of skill in the art, a stringent hybridization can be used to identify or detect identical polynucleotide sequences or to identify or detect similar or related polynucleotide sequences.

As used herein, the term "amplifiable nucleic acid" is used in reference to nucleic acids that may be amplified by any amplification method. It is contemplated that "amplifiable nucleic acid" will usually comprise "sample template."

As used herein, the term "sample template" refers to nucleic acid originating from a sample that is analyzed for the presence of a target sequence of interest. In contrast, "background template" is used in reference to nucleic acid other than sample template which may or may not be present in a sample. Background template is most often inadvertent. It may be the result of carryover, or it may be due to the presence of nucleic acid contaminants sought to be purified away from the sample. For example, nucleic acids from organisms other than those to be detected may be present as background in a test sample.

"Amplification" is defined as the production of additional copies of a nucleic acid sequence and is generally carried out using polymerase chain reaction technologies well known in the art [Dieffenbach C W and G S Dveksler (1995) *PCR Primer, a Laboratory Manual,* Cold Spring Harbor Press, Plainview N.Y.]. As used herein, the term "polymerase chain reaction" ("PCR") refers to the method of K. B. Mullis U.S. Pat. Nos. 4,683,195 and 4,683,202, hereby incorporated by reference, which describe a method for increasing the concentration of a segment of a target sequence in a mixture of genomic DNA without cloning or purification. The length of the amplified segment of the desired target sequence is determined by the relative positions of two oligonucleotide primers with respect to each other, and therefore, this length is a controllable parameter. By virtue of the repeating aspect of the process, the method is referred to as the "polymerase chain reaction" (hereinafter "PCR"). Because the desired amplified segments of the target sequence become the predominant sequences (in terms of concentration) in the mixture, they are said to be "PCR amplified".

With PCR, it is possible to amplify a single copy of a specific target sequence in genomic DNA to a level detectable by several different methodologies (e.g., hybridization with a labeled probe; incorporation of biotinylated primers followed by avidin-enzyme conjugate detection; incorporation of $^{32}$P-labeled deoxynucleotide triphosphates, such as dCTP or dATP, into the amplified segment). In addition to genomic DNA, any oligonucleotide sequence can be amplified with the appropriate set of primer molecules. In particular, the amplified segments created by the PCR process itself are, themselves, efficient templates for subsequent PCR amplifications.

Amplification in PCR requires "PCR reagents" or "PCR materials", which herein are defined as all reagents necessary to carry out amplification except the polymerase, primers and template. PCR reagents normally include nucleic acid precursors (dCTP, dTTP etc.) and buffer.

As used herein, the term "primer" refers to an oligonucleotide, whether occurring naturally as in a purified restriction digest or produced synthetically, that is capable of acting as a point of initiation of synthesis when placed under conditions in which synthesis of a primer extension product that is complementary to a nucleic acid strand is induced, (i.e., in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer and the use of the method.

As used herein, the term "probe" refers to an oligonucleotide (i.e., a sequence of nucleotides), whether occurring naturally as in a purified restriction digest or produced synthetically, recombinantly or by PCR amplification, that is capable of hybridizing to another oligonucleotide of interest. A probe may be single-stranded or double-stranded. Probes are useful in the detection, identification and isolation of particular gene sequences. It is contemplated that any probe used in the present invention will be labelled with any "reporter molecule," so that it is detectable using any detection system, including, but not limited to enzyme (e.g., ELISA, as well as enzyme-based histochemical assays), fluorescent, radioactive, and luminescent systems. It is not intended that the present invention be limited to any particular detection system or label.

As used herein, the terms "restriction endonucleases" and "restriction enzymes" refer to bacterial enzymes, each of which cut double-stranded DNA at or near a specific nucleotide sequence.

DNA molecules are said to have "5' ends" and "3' ends" because mononucleotides are reacted to make oligonucleotides in a manner such that the 5' phosphate of one mononucleotide pentose ring is attached to the 3' oxygen of its neighbor in one direction via a phosphodiester linkage. Therefore, an end of an oligonucleotide is referred to as the "5' end" if its 5' phosphate is not linked to the 3' oxygen of a mononucleotide pentose ring. An end of an oligonucleotide is referred to as the "3' end" if its 3' oxygen is not linked to a 5' phosphate of another mononucleotide pentose ring. As used herein, a nucleic acid sequence, even if internal to a larger oligonucleotide, also may be said to have 5' and 3' ends. In either a linear or circular DNA molecule, discrete elements are referred to as being "upstream" or 5' of the "downstream" or 3' elements. This terminology reflects the fact that transcription proceeds in a 5' to 3' fashion along the DNA strand. The promoter and enhancer elements that direct transcription of a linked gene are generally located 5' or upstream of the coding region. However, enhancer elements can exert their effect even when located 3' of the promoter element and the coding region. Transcription termination and polyadenylation signals are located 3' or downstream of the coding region.

As used herein, the terms "nucleic acid molecule encoding," "DNA sequence encoding," and "DNA encoding" refer to the order or sequence of deoxyribonucleotides along a strand of deoxyribonucleic acid. The order of these deoxyribonucleotides determines the order of amino acids along the polypeptide (protein) chain. The DNA sequence thus codes for the amino acid sequence.

As used herein, the term "antisense" is used in reference to RNA sequences that are complementary to a specific RNA sequence (e.g., mRNA). Antisense RNA may be produced by any method, including synthesis by splicing the gene(s) of interest in a reverse orientation to a viral promoter that permits the synthesis of a coding strand. Once introduced into a cell, this transcribed strand combines with natural mRNA produced by the cell to form duplexes. These duplexes then block either the further transcription of the mRNA or its translation. In this manner, mutant phenotypes may be generated. The term "antisense strand" is used in reference to a nucleic acid strand that is complementary to the "sense" strand. The designation (−) (i.e., "negative") is sometimes used in reference to the antisense strand, with the designation (+) sometimes used in reference to the sense (i.e., "positive") strand.

The term "Southern blot" refers to the analysis of DNA on agarose or acrylamide gels to fractionate the DNA according to size, followed by transfer and immobilization of the DNA from the gel to a solid support, such as nitrocellulose or a nylon membrane. The immobilized DNA is then probed with a labeled oligo-deoxyribonucleotide probe or DNA probe to detect DNA species complementary to the probe used. The DNA may be cleaved with restriction enzymes prior to electrophoresis. Following electrophoresis, the DNA may be partially depurinated and denatured prior to or during transfer to the solid support. Southern blots are a standard tool of molecular biologists [J. Sambrook et al. (1989) *Molecular Cloning: A Laboratory Manual,* Cold Spring Harbor Press, NY, pp 9.31–9.58].

The term "Northern blot" as used herein refers to the analysis of RNA by electrophoresis of RNA on agarose gels to fractionate the RNA according to size followed by transfer of the RNA from the gel to a solid support, such as nitrocellulose or a nylon membrane. The immobilized RNA is then probed with a labeled oligo-deoxyribonucleotide probe or DNA probe to detect RNA species complementary to the probe used. Northern blots are a standard tool of molecular biologists [J. Sambrook, J. et al. (1989) supra, pp 7.39–7.52].

The term "reverse Northern blot" as used herein refers to the analysis of DNA by electrophoresis of DNA on agarose gels to fractionate the DNA on the basis of size followed by transfer of the fractionated DNA from the gel to a solid support, such as nitrocellulose or a nylon membrane. The immobilized DNA is then probed with a labeled oligo-ribonuclotide probe or RNA probe to detect DNA species complementary to the riboprobe used.

The term "isolated" when used in relation to a nucleic acid, as in "an isolated oligonucleotide" refers to a nucleic acid sequence that is identified and separated from at least one contaminant nucleic acid with which it is ordinarily associated in its natural source. Isolated nucleic acid is nucleic acid present in a form or setting that is different from that in which it is found in nature. In contrast, non-isolated nucleic acids are nucleic acids such as DNA and RNA which are found in the state they exist in nature.

As used herein, the term "purified" or "to purify" refers to the removal of undesired components from a sample.

As used herein, the term "substantially purified" refers to molecules, either nucleic or amino acid sequences, that are removed from their natural environment, isolated or separated, and are at least 60% free, preferably 75% free, and most preferably 90% free from other components with which they are naturally associated. An "isolated polynucleotide" is therefore a substantially purified polynucleotide.

As used herein the term "coding region" when used in reference to a structural gene refers to the nucleotide sequences that encode the amino acids found in the nascent polypeptide as a result of translation of a mRNA molecule. The coding region is bounded, in eukaryotes, on the 5' side by the nucleotide triplet "ATG" that encodes the initiator methionine and on the 3' side by one of the three triplets which specify stop codons (i.e., TAA, TAG, TGA).

As used herein, the term "structural gene" refers to a DNA sequence coding for RNA or a protein. In contrast, "regulatory genes" are structural genes that encode products that control the expression of other genes (e.g., transcription factors).

As used herein, the term "gene" means the deoxyribonucleotide sequences comprising the coding region of a structural gene and including sequences located adjacent to the coding region on both the 5' and 3' ends for a distance of about 1 kb on either end such that the gene corresponds to the length of the full-length mRNA. The sequences that are located 5' of the coding region and which are present on the mRNA are referred to as 5' non-translated sequences. The sequences that are located 3' or downstream of the coding region and which are present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene that are transcribed into heterogenous nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

In addition to containing introns, genomic forms of a gene may also include sequences located on both the 5' and 3' end of the sequences that may or may not be present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers that control or influence the transcription of the gene. The 3' flanking region may contain sequences that direct the termination of transcription, posttranscriptional cleavage and polyadenylation.

The term "sample" as used herein is used in its broadest sense and includes environmental and biological samples. Environmental samples include material from the environment such as soil and water. Biological samples may be animal, including, human, fluid (e.g, blood, plasma and serum), solid (e.g., stool), tissue, liquid foods (e.g., milk), and solid foods (e.g., vegetables).

GENERAL DESCRIPTION OF THE INVENTION

The present invention relates to methods and compositions for characterizing the expression patterns of genes and gene families. Specifically, the present invention provides means to generate and monitor gene expression profiles resulting from cellular and physiological changes such that the expression patterns of individual genes or groups of genes can be readily identified and characterized. Importantly, it provides a novel technology that eliminates the cumbersome cloning and sequencing strategies required by the previously developed methods of characterizing gene expression.

Methods of the presently claimed invention, called RAGE (Restriction Analysis of Gene Expression), provide superior means to characterize the gene expression patterns of cells and tissues, identify changes in gene expession responsible for various physiological, developmental, and disease states, and identify and characterize factors that alter gene expression (e.g., drugs). RAGE involves generating or obtaining cDNA from a desired sample, PCR amplifying the cDNA with a degenerate primer set based on conserved motifs of a gene family (e.g., protein families), purifying amplified PCR products that meet appropriate criteria, and, optionally, digesting the purified products with an appropriate set of restriction endonucleases to produce an expression profile. The profile provides expression data for all members of the targeted gene family, including genes that have not been previously identified (i.e., the RAGE method provides a means of identifying new members of gene families). Expression profiles from different samples can be compared (e.g., cancer and non-cancer) to identify differentially expressed genes, to identify a sample as being of a specific type (i.e., comparing the sample to known profiles representing the various potential physiological states of the sample), and to determine the effects of factors (e.g., drugs) on the expression of genes or groups of genes, among other applications. Because of the ease of use, accuracy, sensitivity, and reproducibility of the RAGE method, this technique will find great value in detecting and characterizing molecular alterations in biological samples.

The RAGE approach measures expression levels of individual genes in multigene families for which degenerate primer sets can be created. The multigene families for which RAGE can be applied to include, but are not limited to, protein kinases (such as tyrosine kinases), phosphatases, ligands, receptors, proteases (such as metalloproteases), cytokines (such as interleukins), transmembrane proteins, adapter proteins (such as proteins containing $SH_2$ domains), G protein-coupled receptors (such as the dopamine receptor) and transcription factor families, among others. These families together contain thousands of the genes that play central roles in a wide range of basic cell responses as well as the development of diseases such as cancer. Information on the expression patterns of these key gene families is likely to play a vital role in understanding many processes in normal cell biology and development, as well as oncogenesis.

The RAGE method overcomes many of the shortcomings of the previously developed means of characterizing gene expression and maintains many of their advantages. The RAGE method utilizes a PCR amplification step and can be applied to smaller amounts of starting material than non-PCR based technologies. However, unlike the other PCR-based technologies, RAGE does not require cloning and sequencing of amplified products. Like SAGE and EST sequencing, the RAGE method allows an immediate, unambiguous identification of signals produced by known genes as well as the discovery and measurement of previously unknown genes, but does not require labor-intensive, time-consuming sequencing, and provides the ability to analyze specific gene families rather than all expressed genes. Unlike RAGE, the signals produced by differential displays cannot be quickly assigned to specific genes and, of course, the signals in hybridization based methods are limited to the known sequences the investigator has placed in the array. Like microarray hybridization methods, RAGE allows the parallel processing of a larger number of samples simultaneously. In contrast to the microarray methods, RAGE does not require a significant investment in the generation of a new array each time a new samples are to be tested. Additionally, the RAGE method is scaleable according to the needs and resources of the particular researchers using it. RAGE can be done in any laboratory with a the capability to perform PCR. It is also possible for the method to be utilized on multiple automated devices dedicated to a project attempting to measure the expression levels of thousands of genes in hundreds of samples.

DETAILED DESCRIPTION OF THE INVENTION

The presently claimed invention comprises methods and compositions for identifying expressed genes and comparing expressed genes between samples. More specifically, the present invention identifies expressed genes within a gene family, taking advantage of the known sequences of the gene products from a particular gene family [e.g. protein kinases (such as tyrosine kinases), phosphatases, ligands, receptors, proteases (such as metalloproteases), cytokines (such as interleukins), transmembrane proteins, adapter proteins (such as proteins containing $SH_2$ domains), G protein-coupled receptors (such as the dopamine receptor) and transcription factors] in the design of primers for amplification.

A. Conserved Motifs and Primer Design

Primer design begins by identifying conserved regions or motifs in the known amino acid sequences encoded by genes in multigene families (See e.g., Example 1). Two primers are typically used for amplification by PCR. The present invention contemplates an embodiment where a single primer directed to a single conserved region is employed with a second primer that has i) a random sequence, ii) a poly(dT) or poly(dA) region, or iii) has a sequence corresponding to a restriction enzyme target sequence. In a preferred embodiment, however, the first primer is directed to a first conserved region of a gene in a multigene family and the second primer is directed to a second conserved region of a gene in a multigene family.

It is not intended that the present invention be limited by the nature of the conserved sequence. Ideally, however, the nature of the sequence in the conserved region should be such that there is conservation in the bases used to code the particular amino acids; said another way, it is preferred that the conserved region contains amino acids known to be encoded with limited degeneracy. Amino acids known to be coded with a great deal of degeneracy are serines and leucines. Thus, conserved regions containing serines and leucines (and in some cases arginines) are to be avoided.

It is not intended that the present invention be limited by the length of the conserved sequence. It is preferred, however, that each conserved region comprises greater than three amino acids, and more preferably, greater than five amino acids, and most preferably seven or more amino acids.

In a preferred embodiment, the nature and length of the conserved sequence is controlled such that the region comprises three amino acids known to be encoded with limited degeneracy (e.g., Phe, Tyr, Cys, His, Gln, Glu, Asn, Asp, Lys, Met and Trp) along with three amino acids known to be encoded with considerable degeneracy (e.g., Leu, Ser, Arg, Gly, Pro, Ala, Val, Thr and Ile). Such a conserved region defines a group of oligonucleotide primers of 18 bases (the size of the group of primers depending on the extent of degeneracy and the extent it is desired that all possible sequences are to have corresponding primers).

It is also not intended that the present invention be limited to two conserved regions that are a particular distance apart. A variety of distances in the protein are contemplated. Of course, such distances correspond to distances in the coding sequences of the nucleic acid; a variety of such distances (e.g. between 1 and 2000 bases and more preferably between 80 and 1000 bases) will permit the method of the present invention to successfully identify particular expressed genes in the family. What is important is that the distance between the two conserved regions be known—whatever the size might be. This is important because the present invention contemplates a "pre-step" (which is described below) that allows for the isolation of the desired size amplified product, prior to further manipulation (e.g. restriction digestion).

This is not to say, however, the two conserved regions must be exactly the same distance from one another in every gene of the multigene family (although this is permitted). Indeed, the present invention contemplates that the conserved regions will be within a range of variable distances, when one examines the majority of known genes within a multigene family. Of course, it is not intended that the range be strictly limited. However, distances in the coding sequence that are less than 500 bases and more preferrably less than 200 bases, are contemplated.

Most importantly, various primers that are designed using the above-named steps and approaches can be tested on known templates to evaluate their ability to produce amplicons in a nucleic acid mixture (i.e., in the presence of background template). Primers can be tested (e.g, by mixing a small amount of known template in a genomic DNA) in low and high stringency conditions (defined above) to produce large amounts of amplicon that can thereafter be subjected to gel electrophoresis and isolation (described below). In this manner, the method of the present invention can be evaluated to select primers that will identify differentially expressed gene(s) in various human cell types including intermediate and low abundance transcripts.

B. Amplification and The Size Of The Amplified Product

As noted above, the present invention contemplates amplifying nucleic acid comprising portions of known genes of various multigene families. While a variety of amplification methods can be used (e.g., LCR, Q-beta replicase, etc.), PCR is the preferred amplification method. In the method of the present invention, mRNA is isolated from the sample (and more typically, from two or more samples) and RT-PCR is carried out. That is to say, the mRNA is reverse transcribed into cDNA. Thereafter, the cDNA is amplified with two primers.

From the discussion of the design considerations for primers set forth above it should be clear that PCR will result in amplified product (so-called "amplicon") of a predetermined size range (e.g., 270–285 bp PCR product). This size range is predetermined by the selection of the two conserved regions from the examination of the known sequences of the gene products. By selecting two conserved regions that are found to be (when looking over the various sequences of the various genes) within a relatively small range, the various amplicons will differ in size only by a small amount (e.g., less than 40% of the maximum distance between the to conserved regions and more preferrably less than 20%).

C. Isolating The Desired Amplicon

By knowing the range of size of the amplicon resulting from the amplification step, one can significantly reduce background noise (e.g., caused by the amplification of irrelevant nucleic acid) prior to subsequent steps in the method of the present invention. Specifically, the present invention contemplates an isolation step as a pre-step step to further manipulation. In a preferred embodiment, the total amplicon resulting from the amplification with the above-described primers is run out on a gel under conditions such that the amplicon of different sizes separates. Using appropriate size markers, the predetermined size range can be marked out on the gel and the amplicon falling in that size range can be separated from the rest of the amplicon on the gel. In a preferred embodiment, separation is done simply by cutting out the region of the gel defined by the predetermined size range (e.g., with a razor blade). Thereafter, the desired isolated amplicon can be recovered (e.g., by eluting the DNA from the gel).

D. Identifying The Expressed Gene

Next, the recovered DNA can be used to produce an expression profile for the gene family for the particular cell types tested (e.g., cancer cells and normal cells). In some embodiments of the present invention, restriction enzyme digestion of the samples is used to facilitate reproducible and easy analysis of expression profiles.

Restriction enzymes are chosen that cleave at least one member of the gene family in the amplicon region. Some enzymes (i.e., many 6-hitter—enzymes that digest at 6 nucleotide regions) will not happen to cleave any gene family members in the amplicon. Other enzymes (i.e., many 4-hitters) cut many gene family members and generate many more fragment. The goal is to create a set (e.g., 4 to 25 enzymes) of enzymes that will create at least one and preferably two or more unique fragments for each member of the gene family for unambiguous identification, quantitation, and verification of the gene family expression profile. Temperature of digestion, buffer composition, and nature of the cleavage site (i.e., 3' overhang, 5' overhang, or blunt) are not considerations. The number of enzymes used will vary depending on the size of the gene family. Also a smaller set of enzymes could be used if a user wished to examine only a subset of the gene family.

The digested samples are displayed (e.g., using gel electrophoresis) to produce an expression profile for the tested gene family. Such methods of the present invention have demonstrated excellent reproducibility. Thus, once an expression profile has been generated for a particular sample, the profile can be used as a standard for comparison to future experimental samples (e.g., once an expression profile is generated for a particular gene family in a particular cancer cell, the profile serves as a standard to easily identify such cancer cells from other samples). These methods of the present invention allow characterization of gene expression and identification of particular samples without the need for cloning and sequencing of nucleic acids.

E. Comparing Samples

As noted above, the present invention may be used to compare normal tissue with cancer tissue, as well as to differentiate between cancer tissue that is metastatic and cancer tissue that is non-metastatic. In yet another embodiment, the present invention may be used to detect drug resistance.

The treatment of cancer has been hampered by the fact that there is considerable heterogeneity even within one type of cancer. Some cancers, for example, have the ability to invade tissues and display an aggressive course of growth characterized by metastases. These tumors generally are associated with a poor outcome for the patient. And yet, without a means of identifying such tumors and distinguishing such tumors from non-invasive cancer, the physician is at a loss to change and/or optimize therapy.

With regard to metastatic disease, it is believed that cancer cells proteolytically alter basement membranes underlying epithelia or the endothelial linings of blood and lymphatic vessels, invade through the defects created by proteolysis, and enter the circulatory or lymphatic systems to colonize distant sites. During this process, the secretion of proteolytic enzymes is coupled with increased cellular motility and altered adhesion. After their colonization of distant sites, metastasizing tumor cells proliferate to establish metastatic nodules. The present invention can be used to compare metastatic cancer tissue with non-metastatic cancer tissue to identify differentially expressed genes as markers of metastatic potential. Thereafter, the present invention can be used to determine the presence or absence of these markers in various clinical cancer isolates. The present invention also contemplates "phenotyping" cancer cells adapted to tissue culture.

With regard to drug resistance, it should be noted that success with chemotherapeutics as anticancer agents has been severely hampered by the phenomenon of multiple drug resistance, resistance to a wide range of structurally unrelated cytotoxic anticancer compounds (J. H. Gerlach et al., Cancer Surveys, 5:25 [1986]). The underlying cause of progressive drug resistance may be due to a small population of drug-resistant cells within the tumor (e.g., mutant cells) at the time of diagnosis (J. H. Goldie and Andrew J. Coldman, Cancer Research, 44:3643 [1984]). Treating such a tumor with a single drug first results in a remission, where the tumor shrinks in size as a result of the killing of the predominant drug-sensitive cells. With the drug-sensitive cells gone, the remaining drug-resistant cells continue to multiply and eventually dominate the cell population of the tumor. The present invention can be used to compare drug resistant cells with non-resistant cells to identify differentially expressed genes as markers of drug resistance. Thereafter, the present invention can be used to determine the presence or absence of these markers in various clinical cancer isolates.

The present invention also finds use in drug screening. For example, samples treated with different candidate drugs can be subjected to the methods of the present invention to determine the ability of the compounds to alter gene family members known to be implicated in the disease state. For example, if a particular gene family member is known to be overexpressed in cancer cells (i.e., is identified in the expression profiles of the present invention as a "darker" band compared to normal cells), one can look for drugs that reduce the expression of the suspect gene to normal levels.

Of course the present invention is not limited to the nature of the samples or the nature of the comparison, and will find use in a variety of applications. For example, because the methods of the present invention amplify all members of gene families, previously unidentified gene family members can be identified and characterized. The isolated bands from the amplification reaction can be sequenced and compared to nucleotide databases to determine the novelty of the amplified samples. Samples that do not have homology to known genes likely represent a fragment of new gene family members. The DNA fragment can be used to identify and characterize the full length gene corresponding to the sample using techniques standard in the art.

In another embodiment, the present invention can initially be used to examine the entire gene family expression profile of a particular cell type and physiological condition with the goal of identifying one or a few genes that are predictive of the cell status. For example, an expression profile for a particular type of cancer can be generated. Once this pattern is identified, it may be determined that only one or a few of the gene family members need to be analyzed to identify the cancer. Thus, the sequence of these members can be determined and specific primers can be generated to amplify only these important marker genes. Optionally, at this stage, the RAGE technique can be abandoned and other means of detecting the one or few important markers of the cancerous state can be applied (e.g., antibody assay). In this embodiment, the present invention provides means of identifying predictive marker genes for a given condition.

THE PRESENT INVENTION IN OPERATION

RAGE analysis begins with a degenerate primer set based on conserved motifs in the protein sequence of a gene family. In some embodiments, motifs of just 5 codons or longer (5–7) with spacing of 0.1 to 2 kb are suitable for RAGE, although the present invention comtemplates other configurations. Two conserved motifs are identified and the range of spacing between them within the gene family is noted. For the tyrosine kinase family two motifs were selected in subdomains VII and IX. This abridged alignment of the large tyrosine kinase gene family contains representative members of the tyrosine kinase subfamilies as well as examples of some dual specificity and serine/threonine kinases which share the tyrosine kinase motifs in these regions.

Primer sets derived from these motifs are capable of amplifying the entire tyrosine kinase family as well as an identifiable subset of dual specificity and serine/theronine kinases. Development of the primer sets includes the testing of primers individually and in combinations, as well as determination of appropriate PCR conditions. Once suitable primer sets have been developed, a database containing restriction endonuclease terminal fragment lengths predicted from the corresponding sequence of each gene family member is constructed. Restriction endonucleases with 4 bp and 5 bp recognized sequences are most useful, for each cuts frequently enough to generate fragments from a substantial fraction of the gene family member amplicons. Although enzymes with recognition sites of 6 bp or more could be used (e.g., to identify and measure a single gene family member).

This tyrosine kinase database contains fragments predicted by the use of over 70 enzymes on over 100 human sequences. Two points should be noted. First, a given enzyme cuts only a subset of all the gene family members, often at different locations. Second, for each gene family member, restriction endonucleases can be identified that will generate a fragment length unique to that gene, while other restriction endonucleases may generate fragment lengths that are shared between closely related members of the family. Commercial database software has been modified to generate these databases automatically from inputs of Genbank sequences of gene family members, although the sequences can simply be entered manually in any number of commercially available programs.

Once primer sets and databases have been determined for a gene family, the experimental strategy begins with reverse transcription of an RNA sample utilizing either degenerate gene family primers based on additional conserved motifs 3' to the region to be amplified, or oligo dT. Degenerate gene family reverse transcription primers based motifs of between 3 and 5 codons (9 to 14 bp in length) are easily identified for most gene families. It was found that the use of such primers improves the results by reducing variations, due to different length 3' UT regions in different gene family members, when compared to oligo dT primers. Additionally, samples often containing extensively degraded RNA, such as those obtained from archival pathology specimens, give superior results when using such primers.

After reverse transcription, cDNAs are subjected to PCR amplification using one 5' $^{33}$P end-labelled degenerate primer set and one unlabelled degenerate primer set. The number of cycles and PCR conditions used for each multigene family need to be established and are dependent on the length, base composition and complexity of the primer sets, as well as the expression levels of the multigene family. As an example, for the tyrosine kinase family 5 cycles with a 45° C. annealing temperature are used followed by 2 additional cycles with a 56° C. annealing temperature when starting with 10 ng of input DNA. Following PCR the amplified products are resolved by agarose gel electrophoresis (3% NuSieve agarose [FITC] in 1×TAE buffer at 5 V/cm) and fragments in the range predicted for products of the gene family are excised and extracted (by QIAEXII gel extration kit [Qiagen, Chatsworth Calif.]). The amount of material is determined by liquid scintillation counting and the different samples are then equalized to between 5000 and 50000 dpm/$\mu$l and divided into aliquots.

An aliquot of each sample is then digested with a single restriction endonuclease and a battery of restriction endonucleases can be applied to the aliquots. The digests are resolved by denaturing polyacrylamide gel electrophoresis with suitably constructed size markers, followed by gel drying and exposure of the dried gels to storage phosphor screens and films for autoradiography. The storage phosphor screens are then analyzed by a Molecular Dynamics Pliosphorlmager system allowing use of the large linear detection range ($10^5$) to accurately measure levels of expression.

The present invention initially focused on gene families whose members have previously been shown to play important roles in cancer or other diseases, in gene regulation, and in signal transduction. These include, but are not limited to, serine/threonine kinases, tyrosine phosphatases, metalloproteases, GTPases, Zn finger proteins, G-protein coupled receptors, POU, ETS, and other transcription factor families, TGF beta family ligands, wnt family ligands, as well as numerous others. However, the methods and compositions of the present invention are generally applicaple to the characterization of differences in gene expression between any two samples.

Results and Discussion

Each gel lane contains undigested DNAs at the top derived from gene family members whose amplicons lack the recognition site of the enzyme used. Sub-amplicon length fragments are generated by the various restriction enzymes on particular gene family members containing the recognition site. $^{33}$P is an ideal isotope for use in this system because of its high specific activity and appropriate energy of emission allowing both sensitive detection and high resolution of the fragments by the PhosphorImager/ polyacrylamide gel electrophoresis system. Comparing the display patterns of a gel to the database allows individual fragments to be identified as the products of a specific gene.

The results obtained from the ovarian cancer cell line SK-OV-3, known to contain a amplified erbB2 (neu) allele

(53) show that the fragments produced by digestion of the erbB2 amplicon are readily identifiable and match precisely the ones expected from the database. Several important points should be noted here.

First, since the fragments are end-labelled, the intensity of signals is proportional to the number of molecules, and independent of fragment length, thus the intensity of the erbB2 generated fragments is the same regardless of the particular enzymes used for digestion (when viewing the films it is important to remember the smaller fragments diffuse more and occupy greater area while the larger fragments produce sharper but more intense bands). Here, the advantages of using the PhosphorImager system for accurate and precise quantitation results in a high level of internal consistency when using multiple enzymes for discrete measurements of gene expression levels.

Second, the size of the DNA fragments determined by comparing to the marker corresponds completely with the predicted fragment size. With the current size marker system, measured mobilities differ at most by fractions of a nucleotide base from the predicted mobility and more often exhibit no detectable difference at all. Finally, the accuracy of the size determination, coupled with the use of multiple enzymes, result in the unambiguous identification of the gene family members expressed in a sample. The fraction of bands that cannot be correlated to the database of known family members is dependent on the gene family being studied. For the tyrosine kinase family tested, it was possible to confidently identify the origin of over 80% of the bands in the display, using the existing database of currently known tyrosine kinases.

The unidentified bands can be analyzed by cloning and sequencing methods outlined in the Examples below. Finally, although it may not be completely visible on the reproductions of the films, fragment intensities ranging well over 3 orders of magnitude are detectable and substantially above background. Kinases with expression levels almost $10^{-4}$ times those of the erbB2 kinase can be identified and measured. Identity assignments can be made across this entire range of expression levels, allowing measurement of expression for potentially most members of the gene family in a single gel. Over 40 kinases can be identified and their expression measured.

RAGE is able to detect alterations in expression due to genomic translocations; here the ret proto-oncogene allele in the neuroblastoma cell line SK-N-SH (Lanzi et al., Oncogene 7, 2189 [1992]). Again the assignment of ret is unambiguous and measurements are reproducible across different enzyme digestions. In this figure, predicted restiction fragments of the rearranged RET amplicon are shown on the right-hand side of the figure. Fragments derived from RET in the gel are marked.

RAGE is used to comparatively analyze tyrosine kinase expression levels in a set of 12 samples consisting of representatives of the most commonly occurring human carcinomas accounting for over 80% of the cancer deaths in the U.S. (Table 1). The erbB2 amplification in SK-OV-3, as well as an erbB2 amplification in the breast carcinoma line SK-BR-3 (Kraus et al., EMBO Journal 6, 605), are readily apparent. Some individual kinases ubiquitously expressed in the 12 lines of primarily epithelial origin, as well as individual kinases with a more restricted expression pattern.

TABLE 1

CELL LINES USED IN THESE STUDIES

| 1. CAPAN-1 | Pancreatic adenocarcinoma | 7. SW620 | Colon adenocarcinoma |
|---|---|---|---|
| 2. CAKI-1 | Kidney clear cell carcinoma | 8. SK-N-SH | Neuroblastoma |
| 3. T24 | Bladder carcinoma | 9. U251 | Glioblastoma |
| 4. SK-OV-3 | Ovarian adenocarcinoma | 10. SKMEL28 | Malignant melanoma |
| 5. SK-BR-3 | Breast adenocarcinoma | 11. A549 | Lung carcinoma |
| 6. LnCAP | Prostate adenocarcinoma | 12. NCI-H69 | Small cell lung carcinoma |

Results can be analyzed in several ways. One unit of measurement particularly applicable to RAGE is to calculate the level of expression for an individual gene as a fraction of the level of expression of all amplifiable members of the gene family. By dividing the PhosphorImager units from a particular kinase band by the total number of units loaded into the lane one can eliminate variations due to differences in labelling efficiencies, PCR efficiencies, digestion aliquots, and amounts loaded on the gel. This expression fraction unit is not simply a relative measure, as in array hybridization, but a more absolute measure that can be used to compare results obtained at different times, in different experiments, and in different labs. Variations in the overall transcription levels of a multigene family among samples, although not likely to be large, prevent this fractional measure from being a completely absolute measure of individual gene expression. In practice we have found this type of measurement to be highly reproducible, in different digests, in different samples, and in different experiments. The wide range of functional expression values measured regions use of a logarithmic scale for graphical display of results.

Results can be presented in a variety of formats, such as a profile of gene family expression for SK-OV-3 cells. Thirty-three tyrosine kinases can be detected and their expression levels measured in this single cell line (as well as over 12 kinases of dual specificity or serine/threonine type not shown). In appropriate samples, the methods of the present invention have detected expression by RAGE of nearly every known tyrosine kinase and the results are in excellent agreement with previous reports on patterns of tyrosine kinase expression. For the tyrosine kinase family, RAGE possesses the ability to detect and measure all members of the family and is apparently not skewed to a particular subset of the family.

Results may also be presented in a comparative format, showing the expression patterns of 3 receptor tyrosine kinases across the panel of cell lines. One kinase, FLT, is found in only 2 of the samples, while the other two show more prevalent but significantly differing levels of expression across the panel. These patterns: 1) highly expressed in most samples, 2) expressed at a low level in most samples, and 3) expression limited to only a few cell types in the panel, are seen in RAGE analysis of many other tyrosine kinases across the panel of cell lines.

RAGE Sensitivity

A verification of the results obtained by the RAGE method for the two representative tyrosine kinases is shown. Measurements of expression levels for erbB2 and met obtained by RAGE analysis for the 12 carcinoma lines are compared to measurements obtained by ribonuclease protection assay on the panel. There is excellent agreement between the results obtained by the two methods, with the greatest difference exhibited in the amplified erbB2 allele measurements in the SK-OV-3 and SK-BR-3 cell lines. Here the extreme overexpression of erbB2 (greater than 28% of all tyrosine kinase transcripts in SK-OV-3) is under reported by the RAGE method presumably due to a plateau effect in the PCR due to a depletion from the degenerate primer pool of primers with sufficient homology to erbB2. The RAGE method may be susceptible to under reporting the level of expression for a single highly overexpressed gene from a large multigene family.

A reasonable estimate of the sensitivity of RAGE can be made by noting that tyrosine kinases with expression levels as low as 0.02% of all amplifiable tyrosine kinase transcripts can be detected and measured. Using the Unigene EST database, methods of the present invention found 1,307 ESTs derived from tyrosine kinase genes out of a total of 478,594 total ESTs. Assuming the pool of different libraries from a variety of tissue sources used in the assembly of the Unigene set contains an average level of tyrosine kinase gene expression, tyrosine kinase gene transcripts are then 0.27% of all transcripts within a typical cell. RAGE can thus detect a transcript with a relative abundance of approximately $5 \times 10^{-7}$ (0.02%×0.27%). The ability to measure levels of expression for genes whose transcripts comprise 1 out of 2 million is indeed a significant level of sensitivity, comparing favorably to hybridization based methods. A single experiment can easily detect genes whose transcripts are in the range of 1 in $10^6$ in dozens of samples, a daunting task using sequencing based strategies.

No evidence was found for skewing of the results toward particular genes in the tyrosine kinase family. Many kinases have exhibited as much as a 100-fold range in their expression levels, depending on the sample being analyzed. No individual kinases have been found to be always among the highest or lowest level of expression in all samples tested to date. This lack of preferential amplification may be due to several factors that must be considered when designing RAGE experiments. First, although the primers are highly degenerate (greater than 2000-fold for the tyrosine kinase family) they differ at only a few positions and are overall highly homologous to each other and thus have very similar $T_m$s. The presence of the same 10 bp recognition sequence at the 5' end of the primers also increases the similarity of the $T_m$, particularly in the later higher annealing temperature cycles of the PCR, serving a similar fashion to the anchor sequences in differential display primers. Second, by sequencing hundreds of individual clones generated under RAGE PCR conditions methods of the present invention determined that the temperatures used allowed 2 to 3 bp of mismatch outside the 6 terminal 3' nucleotides. Thus, the available concentration of primers is increased dramatically for each particular cDNA and not limited to those primers with an identical match to the template. Finally, the use of $^{33}$P radiolabelled primers allows the synthesis of smaller quantities of DNA using fewer cycles and incorporating smaller percentages of the primers. Under conditions used for the tyrosine kinase gene family, typically less than 2% of the primers are incorporated into PCR products.

Another concern is complications due to partial digestions of the labelled DNAs. However, the methods of the present invention have not encountered any problems of this nature primarily for two reasons. The first is that the amount of labelled DNA in a digestion is small (ng quantities) and thus it is not difficult to achieve sufficient enzyme activities for complete digestion. Secondly, the DNA being digested is PCR synthesized and thus free from contaminants such as detergents and biological macromolecules, that are inhibitory to digestion of DNAs isolated from biological sources. As a safeguard, the database also contains entries for predicted partial digestion products, allowing a researcher to recognize the problem if it did arise in an experiment.

Applications

The potential applications of the RAGE technique are numerous. Uses of RAGE that have already been made concerning the tyrosine kinase family in human cancers. Results for tyrosine kinase were obtained on a panel of prostatic carcinoma cell lines. These lines have different biological properties and analysis of their patterns of gene expression could provide important clues toward the mechanisms involved. Although the overall kinase expression pattern is similar in these closely related cell lines (as would be expected), significant differences exist. Visible is the complete absence of expression of axl in the LnCAP cell line, in stark contrast to the significant level of axl in the other lines. This absence is due to deletion of the axl locus as verified by Southern blotting. Thus, in addition to amplifications and translocations, under appropriate conditions RAGE is able to detect a third class of genomic alterations, deletions. While the particular genes identified (here tyrosine kinases) may not always play a central role in the process being studied, the identified gene can serve as a marker for the region of the genome where the alteration has occurred, providing useful information on which to base further studies. If a small number of large multigene families, such as protein kinases, are studied by the RAGE method, potentially thousands of markers scattered throughout the genome could be analyzed for evidence of genomic alterations in a rapid and economical fashion with the bonus of acquiring extensive information on the expression patterns of thousands of genes.

An important application of RAGE to current cancer research are the results obtained by the use of RAGE on the tyrosine kinase family in matched pairs of normal and tumor tissue blocks obtained by dissection following radical prostatectomy. The tissue blocks were approximately 50 mg in weight and the tumor blocks were judged to consist of over 80% tumor cells upon pathological examination. Even though the RNA obtained from these samples showed extensive degradation, good results could still be obtained following RAGE analysis. One representative digest out of 18 shows elevation of expression of 2 kinases, NYK (Ling and Kung, Mol. Cell Biol. 15, 6582 [1995]) and CSK, in tumor samples compared to normal. Summarizing the results obtained by the full analysis using the full battery of restriction enzymes, most tyrosine kinases show no significant difference in expression levels in prostate tumor versus normal samples, but in a sense these act as controls for 4 tyrosine kinases we have found to be consistently elevated in prostate carcinomas. For the fourth, RET, the present invention has confirmed the results obtained by RAGE by showing elevation of RET expression at the protein level. The tumor specimens used in the study were of various grades and it is contemplated that further experiments with more samples will determine if there is a correlation between the degree of increased expression of these tyrosine kinases in a specimen and the histological grade of the specimen.

Another application of the RAGE method is to study the effect of exogenously added compounds such as drugs, growth factors, cytokines, or hormones on the profile of gene expression of a cell. The LnCAP prostatic carcinoma cell line shows androgen dependent growth properties. RAGE analysis was performed on tyrosine kinase expression levels on LnCAP cells cultured in media containing androgen depleted serum and on those same cells following addition of physiological concentrations of dihydrotestosterone (DHT). After a full analysis, no significant changes were detected in any of the known tyrosine kinases. However, two bands out of hundreds showed marked elevation in response to DHT. These two bands are derived from the same gene, designated AIK for Androgen Inducible Kinase. This fragment has been cloned and used to obtain a full-length cDNA. The novel gene is not a tyrosine kinase but is a serine/threonine kinase with homology to the MAP kinase family and the cdc2 kinase family. It is one of the subset of serine/threonine kinases that are primed by the tyrosine kinase family primers.

Another use of RAGE in cancer research is in the study of tumor progression. Initial studies on colon tumor progression using a panel of cell lines derived from adenomas, as well as different grades of adenoma carcinomas, both primary and metastatic have been conducted. Normal colon epithelial tissue samples were used as controls. The normal controls are tissue rather than cell cultures and as such contain contaminating cell types of endothelial, hematopoietic, and mesenchymal origin. The contribution of these cell types, though a minor fraction in the sample, can be clearly seen by the presence of many kinase bands in the display lanes of normal tissue, attributable to cells of these types in the normal tissue sample but not the cell line samples. This is further evidence of the specificity and sensitivity of the RAGE method but also illustrates that consideration of sample purity and collection methods are necessary when using RAGE. The apparent slight increase in the expression of many tyrosine kinases genes in the cell line samples compared to normal tissue samples is a reflection of the increased concentration of cells of epithelial origin in the cell lines compared to the normal tissues. However, one band shows a substantial increase in all the colon cancer cell lines compared to normal. This band could arise from one of four known kinases in our database. Further digestions, should reveal the identity of this kinase that may be elevated in colon cancers, or may be an adaptation of colon epithelial cells to in vitro culture.

EXPERIMENTAL

The following examples are provided in order to demonstrate and further illustrate certain preferred embodiments and aspects of the present invention and are not to be construed as limiting the scope thereof.

In the experimental disclosure which follows, the following abbreviations apply: N (normal); M (molar); mM (millimolar); $\mu$M (micromolar); mol (moles); mmol (millimoles); $\mu$mol (micromoles); nmol (nanomoles); pmol (picomoles); g (grams); mg (milligrams); $\mu$g (micrograms); ng (nanograms); l or L (liters); ml (milliliters); $\mu$l (microliters); cm (centimeters); mm (millimeters); $\mu$m (micrometers); nm (nanometers); ° C. (degrees Centigrade); Sigma (Sigma Chemical Co., St. Louis, Mo.); and

Example 1

Identification of Conserved Homology Segments in Multigene Families

Prior to developing degenerate primer sets, conserved motifs in the targeted gene family are identified. Generally, motifs of five codons or longer, and typically five to seven codons, with spacing of 0.1 to 2 kilobases are selected. Motifs can be identified by comparing sequences of a multiple members of gene family. The identification of conserved sequences from a representative set of the gene family allows for the generation of degenerate primers that will amplify all members of the family. Existing on-line databases of protein structure and sequence similarity such as PROSITE (http://www.ebi.ac.uk/searches/prosite.html), Blocks (http://www.blocks.fhcrc.org), Prints (http://www.biochem.ucl.ac.uk/bsm/dbbrowser/prints), ProDom (http://protein.toulouse.inra.fr/prodom.html) and Pfam (http://genome.wustl.edu/eddy/pfam/welcome.html) (D'Esposito et al., Hum. Mol. Genet. 3, 735 [1994]) offer a large battery of candidate families and provide automated means of identifying and aligning motifs. Additionally, sequences can be obtained from a variety of publications that compare and analyze motif conservation among gene families.

In one embodiment, the sequence from a gene family member (e.g., the sequence of a tyrosine kinase) is entered into a publicly available amino acid database search engine (e.g., blast2 available at http://www.bork.embl-heidelberg.de:8080/BLAST2). Search results identify protein sequences from the database that contain regions of homology with the tyrosine kinase. By identifying other family member from the database (e.g., the protein database with contain other sequenced and identified tyrosine kinases), motifs shared among family member are identified. By using the databases listed above (e.g., PROSITE, ProDom, Blocks, Prints, and Pfam) additional family members that contain the motif can be identified.

By repeating the steps above for additional motifs, it is possible to identify several regions of homology amongst gene family members. From these regions, motifs can be selected that are separated by a desired nucleotide spacing to facilitate the RACE technique (e.g., spacing of 0.1 to 2 kilobases). Primers generated from the motifs, can be used in RACE to identify and characterize all members of the gene family. Software (e.g., MacVector 6.01, Oxford Molecular Group, Oxford, England) can be used to help align and identify motifs among sets of genes.

The identification of suitable conserved homology segments for several multigene families is provided below. These examples are used to illustrate methods of identifying conserved motifs, and are in no manner intended to limit the present invention to the specific gene families demonstrated.

I. Tyrosine Kinases

For the tyrosine kinase family, two motifs in subdomains VII and IX were selected. Sequence information for the tyrosine kinases was obtained from published protein kinase sequence data (Hanks and Lindberg, Methods Enzmol. 200, 525 [1991]; Hanks and Quinn, Methods Enzmol. 200, 38 [1991]; and Hanks et al., Science 241, 42 [1988]). This abridged alignment of the otherwise large tyrosine kinase gene family (Hunter, Cell 50, 823 [1987]) contains representative members of the tyrosine kinase subfamilies as well as examples of some dual specificity and serine/threonine kinases that share the tyrosine kinase motifs in these regions. Amino acid sequences from subdomains VII, VIII, and IX are presented. Both the amino and carboxy terminal portions of the shown sequences demonstrate significant homology. Primer sets derived from these motifs were capable of amplifying the entire tyrosine kinase family as well as an identifiable subset of dual specificity and serine/threonine kinases.

II. Tyrosine Phosphatase, POU Transcription Factors, ETS Family, and Serine/Threonine Kinase Families Aligned sequences for gene members of the tyrosine phosphatase, POU transcription factors, ETS, and serine/threonine kinase families are obtained as described above. Primers designed to the two conserved motifs will selectively amplify these, and other gene family members for each respective class.

III. G-Protein, Ras, and TGFβ Families

Aligned sequences for a large number of gene members of the G-protein-coupled receptor, Ras, and TGFβ families are obtained as described above. Candidate positions for degenerate primers are shown below.

Example 2

RAGE Analysis of Tyrosine Kinases

I. General RT-PCR

RNA was isolated by a guanidine isothiocyanate method as described by Chirgwin et al. (Biochemistry 18, 5294 [1979]), although any RNA isolation means is contemplated by the present invention. Fifty micrograms of total cellular RNA was used for reverse transcription, with oligo $(dT)_{12-18}$ as primers. The reaction conditions were as described by Wainstein et al. (Cancer Res. 23, 6049 [1995]). PCR was carried out in 10 mM Tris-HCl (pH 9.3), 50 mM KCl, 2.5 mM $MgCl_2$, 0.1% TRITON X-100, and 200 μM concentrations of each deoxynucleotide triphosphate for 30 cycles, with a cycle profile of 50 seconds at 95° C., 2 minutes at 60° C., and 2 minutes at 72° C., followed by a 7 minute extension at 72° C., using appropriate amplification primers. PCR products were analyzed by 4% PAGE.

II. RT-PCR Profiling of Tyrosine Kinases

The RNA isolation and cDNA synthesis were conducted as described in the previous section except 5 μg of poly(A)+ RNA was used in the initial cDNA synthesis and 20 ng of cDNA was used for each PCR. The PCR primers were derived from conserved motifs identified as explained in Example 1.

The following oligonucleotides were synthesized and purified by polyacrylamide gel electrophoresis (Integrated DNA Technologies) (purification by gel electrophoresis efficiently removes the truncated oligonucleotides that could produce n-1 and n-2 bands in the RAGE procedure):

150 nM TyKi5-16 oligonucleotide 5' end-labelled with $^{33}$P by T4 polynucleotide kinase
75 nM TyKi5-17 oligonucleotide 5' end-labelled with $^{33}$P by T4 polynucleotide kinase
75 nM TyKi5-18 oligonucleotide 5' end-labelled with $^{33}$P by T4 polynucleotide kinase
100 nM TyKi-A3 oligontucleotide
100 nM TyKi-C3 oligonucleotide
100 nM TyKi-G3 oligonucleotide
100 nM TyKi-T3 oligonucleotide
100 nM TyKi-3B oligonucleotide
2 mM $MgCl_2$
200 μM each dNTP
50 mM KCl
20 mM Tris-HCl pH 8.4
10–20 ng cDNA from reverse transcription of RNA sample Tubes containing the above mixtures were placed in a thermocycler and heated to 95° C. for 3 minutes. They were then cooled to 60° C. and 5 units of Taq polymerase was added. 5 cycles of amplification were performed as follows: 94° C. for 1 minute, 56° C. for 1 minute 30 seconds, and 72° C. for 20 seconds plus 2 seconds/cycle.

Following PCR, each PCR reaction was loaded onto a 3% NUSIEVE (FMC BioProducts) agarose gel in 1×TAE buffer with 0.5 μg/ml ethidium bromide and electrophoresed at 5V/cm for 3 hours. Included on the gel was a 100 bp ladder (Life Technologies) in a marker lane. After electrophoresis, bands were visualized under UV illumination. Gel slices containing the tyrosine kinase family band (153–177 bp) were isolated for each sample. The DNA was then extracted from the gel slices with the QIAEX II gel extraction kit (QIAGEN) and eluted from the glass beads with 50 μl 10 mM Tris-HCl pH 8.0. Activity was determined by liquid scintillation counting. The activity of the samples was equalized to 20,000 dpm/μl by dilution with 10 mM Tris-HCl pH 8.0 (5000 to 50000 dpm/μl is acceptable).

```
5' TYKI-11   5'CCAGGTCACCAARRTWDCRGAYTTYGG3'   (SEQ ID NO:1)

5' TYKI-12   5'CCAGGTCACCAARRTWDCYGAYTTYGG3'   (SEQ ID NO:2)

5' TYKI-13   5'CCAGGTCACCAARRTWWGYGAYTTYGG3'   (SEQ ID NO:3)

5' TYKI-14   5'CCAGGTCACCAARRTWGGNGAYTTYGG3'   (SEQ ID NO:4)

5' TYKI-15   5'CCAGGTCACCAARRTIDCNGAYTTYGG3'   (SEQ ID NO:5)

5' TYKI-16   5'CCAGGTCACCAARRTTDCNGAYTTYGG3'   (SEQ ID NO:6)

5' TYKI-17   5'CCAGGTCACCAARRTIWGYGAYTTYGG3'   (SEQ ID NO:7)

5' TYKI-18   5'CCAGGTCACCAARRTTWGYGAYTTYGG3'   (SEQ ID NO:8)

TYKI-A3      5'CACAGGTTACCRHANGMCCAAACRTC3'    (SEQ ID NO:9)

TYKI-C3      5'CACAGGTTACCRHANGMCCACACRTC3'    (SEQ ID NO:10)

TYKI-G3      5'CACAGGTTACCRHANGMCCAGACRTC3'    (SEQ ID NO:11)

TYKI-T3      5'CACAGGTTACCRHANGMCCATACRTC3'    (SEQ ID NO:12)

TYKI-3B      5'CACAGGTTACCRHARCTCCANACRTC3'    (SEQ ID NO:13)
```

PCR conditions for tyrosine kinase RAGE were as below:
70 μl PCR reaction volumes in thin wall 200 μtl tubes containing the following:
50 nM TyKi5-14 oligonucleotide 5' end-labelled with $^{33}$P by T4 polynucleotide kinase
15 nM TyKi5-15 oligonucleotide 5' end-labelled with $^{33}$P by T4 polynucleotide kinase

III. Restriction Digests for Expression Profiling

Restriction digests were performed on the above samples in 10 μl reaction volumes in a 96-well, V-bottom polycarbonate plate. Each reaction consisted of 8.5 μl of $^{33}$P-labelled sample from above, 1 μl of 10× restriction endonuclease buffer supplied by the manufacturer and 0.5 μl of restriction endonuclease at 2 to 10 units/μl. Digestions were incubated for 45 minutes at the temperature specified by the supplier of the restriction endonuclease. Following incubation, 6.7 μl of stop/loading buffer (95% deionized formamide, 10 mM EDTA pH 8.0, 0.01% bromphenol blue, 0.01% xylene cynol) was added to each digestion and mixed thoroughly. The digested DNAs were then denatured at 75° C. for 6 minutes. 4 μl of each digest was then loaded into a well formed sequencing gel apparatus (Life Technologies). The DNA was then electrophoresed at 50W in a 6% acrylamide gel (19:1 acrylamide/bis-acrylamide) containing 6M urea and 0.5×TBE buffer.

Following electrophoresis, the gels were fixed in a solution of 10% methanol/5% acetic acid for 15 minutes. After drying, the gels were exposed to a storage phosphor screen (Molecular Dynamics) for 24 hours and the screens were analyzed on a PHOSPHORIMAGER (Molecular Dynamics).

Example 3

Generation of Expression Profile Database

To facilitate widespread use of the RAGE, databases should be created to allow interpretation of the restriction fragment data collected. The tyrosine kinase database that has been constructed can be further completed by three methods. The first will be inclusion of EST sequence data for tyrosine kinase genes for which a complete cDNA has not been reported. This will be accomplished by both keyword and homology search methods and is straightforward. The second method is by cloning and sequencing the unidentified bands that appear in the analysis of the 60 NCI cancer lines. The present invention provides an efficient method for this. The method is based on RACE cDNA cloning procedures (Chenchik et al., Biotechniques 21, 526 [1996]; and Frohman et al., Proc. Natl. Acad. Sci. 85, 8998 [1988]) and works for fragments that appear in any restriction enzyme digest regardless of terminal structure of the cleavage site. This method has been used to identify the androgen inducible kinase (AIK) discussed above, as well as four other novel kinases shown in Table 2. This method can be applied to the unidentified bands that appear during the analysis of the wider spectrum of cell types in the NCI 60 cell line panel.

TABLE 2

| CLONING AND IDENTIFICATION OF NOVEL KINASES | |
|---|---|
| CLK4 | DFGSATYDDEHHSTLVSTRHYRAPEVILALGWAHRC |
| CLK5 | DFGSARFDHEHHSTIVSTRHYR |
| STE20-LIKE | DFGSASMASPANSFVGTPYWMAPEVIAMDEGQYDG |
| NK88 | DFGLAREIQSRPPYTDYLSTRWYRAPELLLRSTNYSS |

Finally, the database will be further refined by incorporation of base composition and terminal 3' nucleotide information known to affect fragment mobilities slightly (Takahashi et al., Mutat. Res. 234, 61 [1997]). Although there is now excellent agreement between observed mobilities and those predicted from the database, this improvement should allow easier more precise analysis of the results. This database structure will then be used in the construction of databases for other gene families.

Example 4

Refining Primer Design

Several efforts can be taken to optimize the primer design for use in RAGE analysis. Such methods include:

i) Selection of highly conserved blocks of sequence in the gene family with attention to the codon redundancy and GC content.

ii) Division of the reverse translated sequences into pools for DNA synthesis to ensure nearly equal representation of each desired sequence, avoiding a single highly degenerate synthesis, which assumes equal coupling efficiencies of the different nucleotides at redundant positions.

iii) Polyacrylamide gel electrophoresis purification of the primers to be 5' labelled by $^{33}$P. This is necessary to avoid the appearance of the faint n-1 and n-2 bands in the display pattern.

iv) Testing the primers under various PCR conditions for the ability to generate a PCR amplicon of the predicted size as assayed by agarose gel electrophoresis as described herein.

v) Testing of the primers individually and in combination to create a set that amplifies a total pattern similar to the sum of the individual primers for each end of the amplicon as described herein. 5' primers differing in their sequences 9–12 bases from the 3' end (4th codon) A, B, C, D, E and a mixture of all 5 oligos are used for RAGE analysis of tyrosine kinase expression in a single sample. The total lane is nearly the sum of the individual primers and contains no additional bands.

vi) Sequencina of a pool of clones generated from the gene family amplicon to identify the composition of the pool in terms of spectrum of the family represented, number, and type of sequences outside the family (and entry of those sequences into the predicted restriction fragment database), and degree of mismatch allowed at the priming sites under the PCR conditions used. This can be done according to the rapid cloning and sequencing strategy as described by Robinson et al. (Proc. Natl. Acad. Sci. 93, 5958 [1996]).

vii) Testing of the number of cycles needed to generate a sufficient amount of material for RAGE analysis, and testing by RAGE analysis that the expression pattern is not affected by cycle number in the range to be used to avoid plateau effects. A single sample of PCR amplified and aliquots are removed following 21, 25, and 29 cycles. After equalization of the activities in each aliquot by dilution of the aliquots from the higher number of cycles, they are digested and electrophoresed. No significant difference in the patterns exists indicating that the results were not being skewed across this range of cycles.

Example 5

Fluorescence Detection Methods in Laser Based Automated Sequencing Devices

The tyrosine kinase gene family RAGE analysis discussed above can be used to determine suitable parameters for the use of laser-based automated sequencing devices in RAGE analysis. The potential advantages of these systems are increased throughput and a larger range of readable fragment lengths. Just as in sequencing applications the longer read length would allow more fragments to be analyzed in a single run increasing the amount of extractable data. First, several different florescent dyes which can be attached at the 5' end of oligonucleotides can be evaluated. 6-FAM, HEX and TET labelled tyrosine kinase primers using samples from the cell line panel already characterized by the $^{33}$P-labeling method can first be evaluated on the Perkin Elmer ABI PRISM multidye system. Next, the GENESCAN software package can be used for size determination and quantitation of band intensities and the results can be compared with the results from $^{33}$p labeling method. Next, on the Pharmacia ALF Express system, the present invention can initially use Cy5 as the label and the quantitation software available on that system. At this point, it will be necessary to test several conditions in concert on both systems. Particularly, gel loading amounts and machine baseline and gain settings must be optimized (McIndoe et al., Electophoresis 17, 652 [1996]). Typically settings that may be optimal for detecting bands of roughly equal intensities in a sequencing gel may not be suitable for the accurate measurement of bands ranging across almost three orders of magnitude in a RAGE gel.

Further experiments on the multi-dye system will test the use of multiple dyes in the same lane either as the same digest of different samples or different digests of the same sample. The results will be compared to single dye results and also $^{33}$P results. It may be anticipated that two dyes with overlapping emission spectra may not give satisfactory quantitative results when the same digest of two different samples are loaded into the same lane. This would produce many co-migrating bands and the signal obtained from a high expression level of a kinase in one sample might be expected to complicate measurement of the intensity of the same kinase band in the sample with a lower level of expression. Along similar lines, the present invention can test the feasibility of using an in-lane size marker and the effects on accuracy of size determination and quantitation. Finally, currently existing database programs can be altered to accept output files of the type generated by the GENESCAN software to rapidly analyze the resulting expression data.

Other means of automating the methods of the present invention as will be known to those skilled in the art are also contemplated by the present invention.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in material science, chemistry, and molecular biology or related fields are intended to be within the scope of the following claims.

We claim:

1. A method, comprising:
   a) providing: i) a sample containing nucleic acid, ii) a first primer having a sequence of which at least a portion is at least partially complementary to a first conserved region of a gene from a multigene family, iii) a second primer having a sequence of which at least a portion is at least partially complementary to a second conserved region from said gene of said multigene family, said first and second conserved regions separated in each gene by a distance, said distance varying between a minimum distance and a maximum distance, said maximum distance differing by said minimum distance by less than 500 bases and iv) a polymerase and PCR reagents;
   b) preparing said nucleic acid from said sample under conditions so as to produce amplifiable nucleic acid;
   c) amplifying said nucleic acid with said first and second primers, said polymerase and said PCR reagents under conditions such that multiple amplified products are generated;
   d) isolating a portion of said amplified products to create a fragment mixture, said fragment mixture containing three or more amplified products in a size range, said range defined by a lower end and a higher end, said lower end defined by approximately said minimum distance and said higher end defined by approximately said maximum distance; and
   e) treating said fragment mixture with a plurality of restriction enzymes.

2. The method of claim 1, wherein said maximum distance is less than 2000 bases.

3. The method of claim 1, wherein said maximum distance differs from said minimum distance by less than 40% of said maximum distance.

4. The method of claim 1, wherein a portion of said first primer is completely complementary to a first conserved region and a portion of said second primer is completely complementary to a second conserved region.

5. The method of claim 1, wherein said preparing of step (b) comprises isolating mRNA.

6. The method of claim 6, wherein said preparing further comprises preparing cDNA from said mRNA.

7. The method of claim 1, wherein said isolating of step (d) comprises electrophoresing said multiple amplified products on a gel.

8. The method of claim 7, wherein said isolating further comprises removing said multiple amplified products in said size range from said gel, thereby separating said multiple amplified products in said size range from amplified products not in said size range.

9. The method of claim 1, wherein said gene is from a multigene family selected from the group consisting of protein kinases, phosphatases, ligands, receptors, proteases, cytokines, transmembrane proteins, adapter proteins, G protein-coupled receptors and transcription factors.

10. A method of analyzing expressed genes in biological samples, comprising:
    a) providing: i) two samples containing mRNA, ii) a first primer having a sequence of which at least a portion is at least partially complementary to a first conserved region of genes from a multigene family, iii) a second primer having a sequence of which at least a portion is at least partially complementary to a second conserved region of said genes from said multigene family, said first and second conserved regions separated in each gene by a distance, said distance varying between a minimum distance and a maximum distance among said genes in said multigene family, said maximum distance differing by said minimum distance by less than 500 bases and, iv) a polymerase and PCR reagents;
    b) treating said mRNA of each of said two samples under conditions so as to produce amplifiable DNA from each sample;
    c) amplifying said amplifiable DNA from each sample with said first and second primers, said polymerase and said PCR reagents under conditions such that multiple amplified products are generated from each of said two samples;
    d) electrophoresing said multiple amplified products from each of said two samples on a gel;
    e) isolating a portion of said amplified products to create a fragment mixture, said fragment mixture containing three or more amplified products from each of said two samples in a size range, said range defined by a lower end and a higher end, said lower end defined by approximately said minimum distance and said higher end defined by approximately said maximum distance; and
    f) treating said fragment mixture with a plurality of restriction enzymes.

11. The method of claim 10, wherein said maximum distance is less than 2000 bases.

12. The method of claim 10, wherein said maximum distance differs from said minimum distance by less than 40% of said maximum distance.

13. The method of claim 10, wherein a portion of said first primer is completely complementary to a first conserved region and a portion of said second primer is completely complementary to a second conserved region.

14. The method of claim 10, wherein said preparing of step (b) comprises isolating mRNA.

15. The method of claim 14, wherein said preparing further comprises preparing cDNA from said mRNA.

16. The method of claim 10, wherein said isolating of step (d) comprises electrophoresing said amplified products on a gel.

17. The method of claim 16, wherein said isolating further comprises removing said multiple amplified products in said size range from said gel, thereby separating said multiple amplified products in said size range from amplified products not in said size range.

18. A method for generating an expression profile standard, comprising:
  a) providing: i) a sample containing nucleic acid, ii) a first primer having a sequence of which at least a portion is at least partially complementary to a first conserved region of a gene from a multigene family, iii) a second primer having a sequence of which at least a portion is at least partially complementary to a second conserved region from said gene of said multigene family, said first and second conserved regions separated in each gene by a distance, said distance varying between a minimum distance and a maximum distance, said maximum distance differing by said minimum distance by less than 500 bases and iv) a polymerase and PCR reagents;
  b) preparing said nucleic acid from said sample under conditions so as to produce amplifiable nucleic acid;
  c) amplifying said nucleic acid with said first and second primers, said polymerase and said PCR reagents under conditions such that multiple amplified products are generated;
  d) isolating a portion of said amplified products to create a fragment mixture, said fragment mixture containing three or more amplified products in a size range, said range defined by a lower end and a higher end, said lower end defined by products approximately said minimum distance and said higher end defined by approximately said maximum distance; and
  e) treating said fragment mixture with a plurality of restriction enzymes.

19. A kit comprising first and second oligonucleotide primers, said first oligonucleotide primer specific for a first conserved region of a gene of a multigene family and said second oligonucleotide primer specific for a second conserved region of said gene from said multigene family, said first and second conserved regions separated in each gene by a distance, and an expression profile standard generated by the method of claim 18.

* * * * *